United States Patent
Alvarez et al.

(10) Patent No.: US 10,161,842 B2
(45) Date of Patent: Dec. 25, 2018

(54) SCANNING RHEOMETER

(71) Applicant: Danmarks Tekniske Universitet, Lyngby (DK)

(72) Inventors: Nicolas Javier Alvarez, Philadelphia, PA (US); Ole Hassager, Frederiksberg (DK)

(73) Assignee: Danmarks Tekniske Universitet, Lyngby (DK)

( * ) Notice: Subject to any disclaimer, the term of this patent is extended or adjusted under 35 U.S.C. 154(b) by 78 days.

(21) Appl. No.: 15/127,682

(22) PCT Filed: Mar. 26, 2015

(86) PCT No.: PCT/EP2015/056515
§ 371 (c)(1),
(2) Date: Sep. 20, 2016

(87) PCT Pub. No.: WO2015/144806
PCT Pub. Date: Oct. 1, 2015

(65) Prior Publication Data
US 2017/0138830 A1  May 18, 2017

(30) Foreign Application Priority Data

Mar. 26, 2014 (EP) .................................. 14161675

(51) Int. Cl.
*G01N 11/00* (2006.01)
*G01N 13/02* (2006.01)
*G01B 11/08* (2006.01)

(52) U.S. Cl.
CPC .............. *G01N 11/00* (2013.01); *G01B 11/08* (2013.01); *G01N 13/02* (2013.01); *G01N 2011/004* (2013.01)

(58) Field of Classification Search
CPC ................. G01N 11/00; G01N 33/442; G01N 2011/0026; G01N 2011/004; G01N 2203/0092; G01N 2203/0094; G01B 11/08
See application file for complete search history.

(56) References Cited

U.S. PATENT DOCUMENTS

| | | |
|---|---|---|
| 6,711,941 B2 | 3/2004 | Braithwaite et al. |
| 2002/0116987 A1 | 8/2002 | Braithwaite et al. |

(Continued)

FOREIGN PATENT DOCUMENTS

| | | |
|---|---|---|
| WO | WO 02/14836 A2 | 2/2002 |
| WO | WO 03/004998 A1 | 1/2003 |
| WO | WO 10/013066 | 2/2010 |

OTHER PUBLICATIONS

Anders Bach et al.: Growth of non-axisymmetric disturbances . . . , 2002.

(Continued)

*Primary Examiner* — Blake A Tankersley
(74) *Attorney, Agent, or Firm* — Hamilton, Brook, Smith & Reynolds, P.C.

(57) ABSTRACT

The present disclosure relates to a filament stretching rheometer for measuring rheological and/or mechanical properties of a sample, comprising: a pair of opposed surfaces for holding the sample therebetween; an actuator configured to provide a controlled axial displacement of at least one of said opposed surfaces; and a sample scanning unit for measuring a diameter of said sample, the sample scanning unit configured for measuring said sample diameter at an axial position controlled independently of the displacement of the opposed surfaces, the sample scanning unit configured for being positioned at a starting point before said controlled axial displacement, wherein the starting point is selected (Continued)

from a position where a minimum diameter of the said sample is determined by said sample scanning unit.

13 Claims, 5 Drawing Sheets

(56) References Cited

U.S. PATENT DOCUMENTS

2003/0051533 A1   3/2003   James et al.
2005/0132783 A1   6/2005   Reinheimer et al.
2012/0234081 A1   9/2012   Maia et al.

OTHER PUBLICATIONS

Anders Bach et al; Extensional viscosity for polymer melts measured in the filament straching rheometer; Journal of Rheology, Society og Rheology, US, vol. 47. No. 2, Mar. 1, 2003.
Roger Yeh; Closed-loop controlled filament stretching and Break-up of Polymer Solutions, Jun. 2005.

SCANNING RHEOMETER

This application is the U.S. National Stage of International Application No. PCT/EP2015/056515, filed Mar. 26, 2015, which designates the U.S., published in English, and claims priority under 35 U.S.C. §§ 119 or 365(c) to European Application No. 14161675.5, filed Mar. 26, 2014. The entire teachings of the above applications are incorporated herein by reference.

FIELD OF INVENTION

The present disclosure relates to rheology and more strictly under the sub-field of extensional rheology. Rheology is the measurement of a simple or complex (colloidal suspension, adhesives, paints, foods, or melt) fluid's response to a specified kinematic flow. The present disclosure relates to an apparatus that can measure extensional rheological properties and in particular the extensional rheological properties of polymer melts and concentrated polymer solutions.

BACKGROUND OF INVENTION

Extensional flows dominate industrial processes, however, the response of materials in such flow fields are poorly understood. This is mostly attributed to the difficulty in designing an apparatus to strictly measure extensional properties.

Whereas several instruments are commercially available to measure the shear properties of such complex fluids, there are very few commercially available instruments for the measurement of extensional properties. The working principle of an extensional rheometer is analogous to the shear (torsional) rheometer. In a shear rheometer, a quantity of sample is placed between two plates (flat, coned, annular, etc.) and one or both plates are rotated at a constant rate, stress, or oscillated at a prescribed frequency. Through careful measurement of the torque required to rotate the disk(s) or the resulting strain of the material given a prescribed torque, it is possible to determine a shear viscosity as a function of stress, strain, or frequency.

The same concepts apply to an extensional rheometer. However, instead of applying a simple shear flow between two plates, the extensional rheometer applies a stretching flow. The principle underlying extensional flow is that a sample is stretched such that its cross sectional area is decreasing in time. Here lies the difficulty in applying a well-defined extensional flow, since applying a constant extensional strainrate or stress to a material requires controlling how the material's cross sectional area is changing in time. This is fundamentally different than a shear rheometer, where the cross sectional area is constant in time.

The majority of materials made from polymers have properties that are neither completely solid-like (elastic) nor completely fluid-like (viscous). These materials are often referred to as "soft" materials or "complex" fluids ("complex" due to their complex molecular structure). From a mechanical perspective these materials are referred to as viscoelastic. A complete description of viscoelasticity is far from complete, however, in the limit of small deformations, i.e. close to equilibrium, there exists a framework called the theory of linear viscoelasticity. In this limit, a material has precisely the same rheological response in both shear and extension. Therefore, this limit acts as a superb test for the working principle of any design of an extensional rheometer. Outside the small deformation limit, known as the nonlinear viscoelastic response, which is more relevant to industrial processing flows, shear and extensional rheological properties are fundamentally different and in some cases completely opposite, i.e., shear thinning and extension thickening. Thus the nonlinear shear properties of complex fluids alone are insufficient and irrelevant to characterizing, predicting, and controlling complex fluids in industrially relevant flows. Therefore, a technique that can measure accurately and quantitatively the linear and nonlinear viscoelastic extensional properties of complex materials would be invaluable.

Despite academic and industrial interests and attempts in measuring extensional properties of complex fluids, very few methods are commercially available that provide absolute quantitative parameters. Most methods do not actively monitor the strain of material and instead correlate strain from a mechanical motion. This assumption is not always valid, prevents the ability to obtain steady state rheological properties, and can easily lead to erroneous irreproducible results.

In so-called filament stretching rheometers (FSR), the strain is a direct measurement via in-situ measurement of the mid-filament diameter via optical techniques. There have been many designs over the years to ensure the measurement of the mid-filament diameter.

One solution has been to design an FSR with an optical measuring device to a fixed diameter measuring point, from where both plates moved symmetrically. Another solution has been to equip an FSR with an optical measuring device to a moving stage, and linking this to the movement of one of the plates, such that only the mid-filament diameter was measured.

The mid-filament diameter, which per se is the diameter measured mid between the two plates, can be used to determine rheological properties, in ideal cases where mid-filament diameter is the minimum diameter. For some materials, this is indeed the case, but for polymer melts and solutions, this is not always the case. Due to gravity, the minimum diameter may be below the mid-filament diameter. This effect is referred to as the sagging effect. By measuring the mid-filament diameter, where sagging occurs, the rheological properties may be miscalculated.

What is missing is a device, in particular an FSR, for measuring theological properties of materials, in particular polymer melts and solutions, where the sagging effect is taken into account.

Furthermore, in FSRs, measuring or knowing the strain is not enough. For an extensional rheometer to be useful it must be capable of prescribing a well-defined rheological flow, such as constant uniaxial extension and/or constant stress. In the working principle of the FSR, a movement of the plates, suspending the material, correlates to a decrease or increase of the diameter. This correlation/relationship depends on the material being measured, the measurement temperature and the strain-rate or stress applied. Not surprisingly, this correlation/relationship is almost never known a priori: making it very difficult to apply a well-defined rheological flow.

Two approaches have been taken to overcome this hurdle. The first method uses an open-loop control scheme to determine the correlation/relationship, while the second method avoids it using a closed loop feedback control. FSR designs that use open-loop feedback control require a great deal of experimental iteration: wasting sample and time.

FSR designs that use closed-loop feedback control require a link between the measured mid-filament diameter and the movement. If the mid-filament diameter however is different from the minimum diameter, according to the sagging effect, the rheological flow may end up being wrong.

What is missing is an FSR with closed-loop control with the ability to measure a variety of extensional rheological properties of complex fluids where the sagging effect is taken into account.

SUMMARY OF INVENTION

In order to solve the above described problems, the present disclosure is providing a filament stretching rheometer for measuring rheological and/or mechanical properties of a sample, comprising: a pair of opposed surfaces for holding the sample therebetween; an actuator configured to provide a controlled axial displacement of at least one of said opposed surfaces; and a sample scanning unit for measuring a diameter of said sample. The sample scanning unit is preferably configured to select a starting point which corresponds to the axial position of the minimum diameter of the sample. In a further embodiment the sample scanning unit may be configured for measuring said sample diameter at an axial position controlled independently of the displacement of the opposed surfaces, the sample scanning unit configured for being positioned at a starting point before said controlled axial displacement, wherein the starting point is selected from a position where a minimum diameter of the said sample is determined by said sample scanning unit.

According to the present disclosure, the sample scanning unit is responsible for providing an FSR, where the sagging effect is taken into account. That is, if a sample is sagging, i.e. its minimum diameter is not exactly at the midpoint between the pair of opposed surfaces, then the sample scanning unit may be able to measure the diameter of the sample at various axial positions below the midpoint, at the midpoint and above the midpoint. Accordingly, the starting point may be at various axial positions below the midpoint, at the midpoint and above the midpoint.

By having the sample scanning unit configured for measuring said sample diameter at an axial position controlled independently of the displacement of the opposed surfaces, there need to be no gearing or other type of coupling between the axial displacement of the opposed surface(s) and the sample scanning unit. In this regard, a gearing or other type of coupling may be avoided, thus providing a less constrained, or rather a more flexible FSR. Furthermore, it is by having the sample scanning unit configured for measuring said sample diameter at an axial position controlled independently of the displacement of the opposed surfaces, that the problem related to sagging can be solved.

One purpose of the present disclosure is to determine the minimum diameter of the sample regardless of the sample is sagging or not. Accordingly, the sample scanning unit may be configured for obtaining a diameter profile of the sample. Furthermore, the sample scanning unit may be configured to determine the minimum diameter of the sample before, during, and/or after said controlled axial surface displacement. In this way, the minimum diameter may for example be determined from the diameter profile of the sample.

One advantage of the present disclosure is that not only the diameter, but the diameter profile of the sample may be used to determine rheological properties of the sample. Furthermore, since the sample scanning unit may be configured to determine the minimum diameter of the sample before, during, and/or after said controlled axial surface displacement, the diameter profiles or minimum diameter as obtained before, during, and/or after said controlled axial surface displacement may be compared. This comparison may be used to determine other properties of the sample, in particular mechanical properties such as Poisson's ratio, Young's modulus and/or tensile strength. These other properties may be determined from a data processor, either by real-time processing or by post-processing the data of diameter profiles.

As can be understood from the present disclosure, the minimum diameter may not necessarily be obtained from a single measurement, but rather from a set of measurements. In this regard, there may be means for determining the minimum diameter from a set of measurements of diameters, and therefore the sample scanning unit may be configured to provide recorded data to a data processor configured for selecting a minimum value from a set of data, in particular a computer, or a hardware chip, such as an FPGA chip. The operation of determining a minimum from a set of data may be a fast operation. Thus, the measurement of the minimum diameter may accordingly be fast and therefore related to a real-time process.

Due to real-time processing, and thereby fast determination of the minimum diameter, it may be possible to implement closed-loop feedback control and thus measure a variety of extensional rheological properties of complex fluids. Accordingly, there may be a feedback controller configured to control the actuator based on input from the sample scanning unit. In this way, the present disclosure provides an FSR with closed-loop control with the ability to measure a variety of extensional rheological properties of complex fluids where the sagging effect is taken into account.

The present disclosure provides further an FSR which actively controls the stress, strain-rate, and overall kinematic flow fields of a material in extension: making it possible to measure both transient and steady responses of extensional stress, strain, strain-rate, and viscosity.

According to the present disclosure, one purpose of the present disclosure is to measure extensional rheological properties of complex fluids in a compact tabletop design via a closed-loop control scheme and the working principle of an active FSR: ensuring accurate reliable measurements of transient and steady state viscosity, stress, and strain, which results in accurate measurements of creep compliance, the elastic and viscous modulus, extensional viscosity, Young's Modulus, Poisson Ratio, strain at break, linear viscoelasticity, and relaxation times.

Another purpose of the present disclosure is to measure mechanical properties of solids, particular in tension, but also in compression.

In a second aspect of the present invention is provided an environmentally controlled chamber for a filament stretching rheometer, comprising an insolating surface configured to be placed around a sample, and such that said surface can be removed from said sample by displacing said surface, thereby exposing said sample to ambient conditions.

In a third aspect of the present invention is provided a method for controlling a filament stretching rheometer, comprising the steps of: stretching a sample between two opposed surfaces such that said sample is fixed in an initial state, and said two opposed surfaces are in fixed positions; measuring a plurality of diameters of said sample in said initial state in a plurality of positions between said opposed surfaces in said fixed positions with a moving sample scanning unit, thereby moving said sample scanning unit independently of said two opposed surfaces; determining a minimum diameter from said plurality of diameters; and selecting a starting point of said moving sample scanning unit for a measurement from said minimum diameter.

DETAILED DESCRIPTION OF THE INVENTION

The present disclosure relates to a filament stretching rheometer for measuring rheological and/or mechanical properties of a sample.

Figure 1:
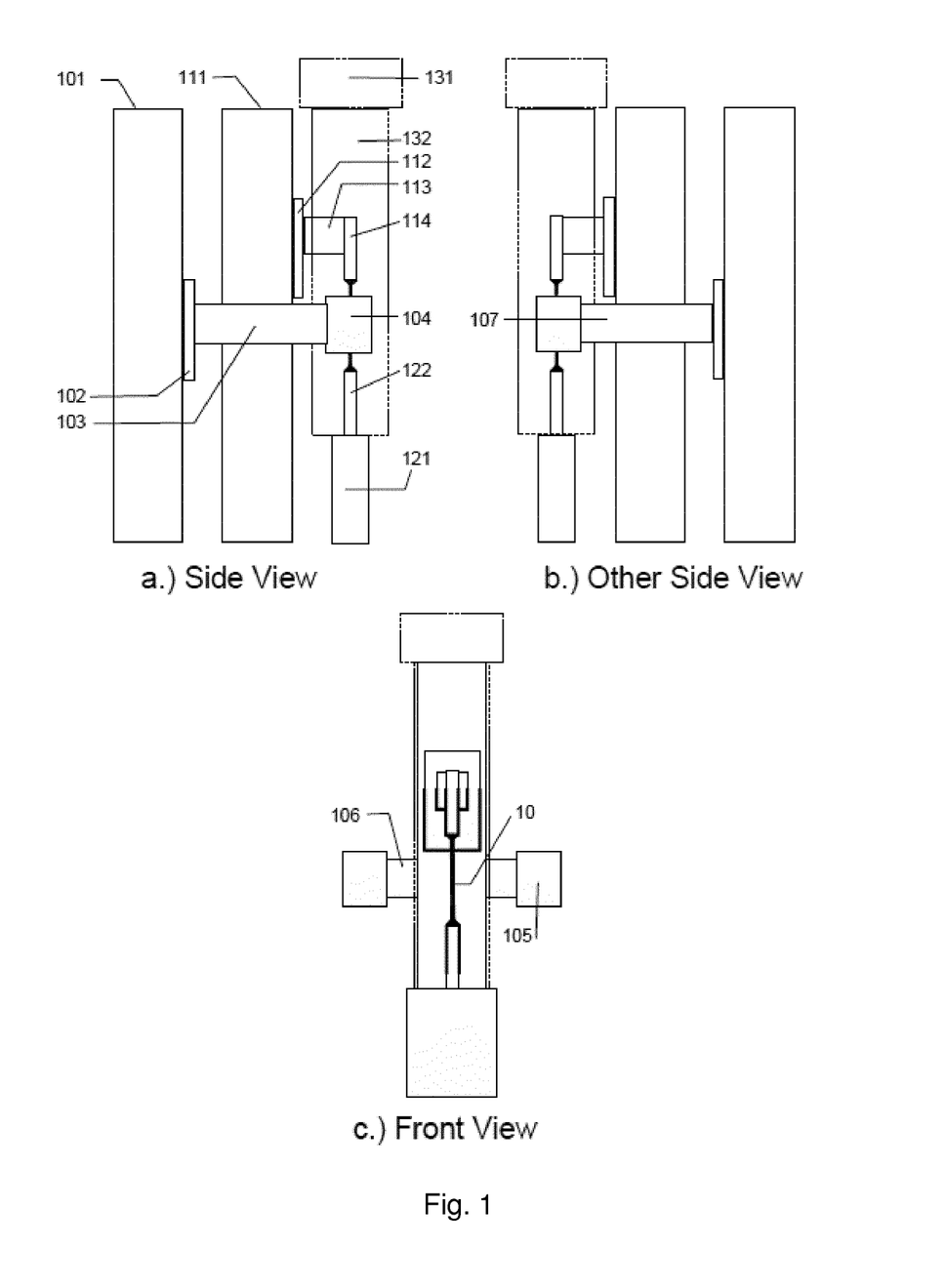
FIG. 1 shows a schematic illustration of one embodiment of the scanning rheometer according to the present disclosure, from a view as follows: a) side-view, b) opposite side-view, and c) front-view.

Referring to FIG. 1, there is a motor 101 with a moving plate 102 connected to a light source 104 and a detector 105 via arms 103 and 107 and crossbar connector 106, a second motor 111 with a moving plate 112 connected to a top surface 114 via connector 113, a bottom surface 122 connected to a force/pressure transducer 121, and a housing 132 that surround the top surface 114, bottom surface 122 and sample 10 and controls environmental conditions of sample via controller 131.

Opposed Surfaces

The two opposed surfaces, top 114 and bottom 122, create opposed surfaces, for which the sample 10 is suspended. The opposing surfaces may be surfaces on a pair of opposed plates or rods and be constructed of any material. Furthermore, the material comprising the surfaces may be roughened, polished, or chemically coated to promote adhesion of the sample to the surfaces. The shape of the opposing surfaces may be square, circular, rectangular, elliptical, or 3-dimensional structures, e.g. spherical or conical, or any 3-dimensional structures. The size of the opposed surfaces may be a wide range depending upon the application, materials, and the embodiment of the invention.

The shapes and sizes of the opposing surfaces need not be the same and may be any combination of shape and size. The preferred orientation of the surfaces may be parallel to each other, but need not be, and depending on application, the surfaces may have other orientations. The two surfaces, top 114 and bottom 122, may be interchangeable.

Sample

The sample may be melts and solids. Typical samples may be Polystyrene, Polymethylmethacrylate, Polyethylene, Polycarbonate, Polypropylene, Polylsoprene, and/or Polybutylacrylate. All samples may have a glass transition temperature and/or a melting temperature. One purpose of the present disclosure is to measure some properties below the glass transition temperature and/or melting temperature of the samples after it has been stretched.

The size of the sample depends on how the sample is stretched. Accordingly, the size and shape of the sample suspended between the two surfaces depends on the size, shape, separation, trajectory of separation, and orientation of the two opposed surfaces.

Sample Scanning Unit

In one embodiment of the present disclosure, the sample scanning unit is configured for moving independently of the axial displacement of the opposed surface(s). It is because of this configuration, that the sample scanning unit may be able to determine the minimum diameter of the sample before, during, and/or after said controlled axial surface displacement.

As previously described, the sample scanning unit may be configured to determine the minimum diameter of the sample before, during, and/or after said controlled axial surface displacement. Accordingly, the scanning unit may be configured for operation before, during and/or after the displacement of said opposed surface(s).

In one embodiment of the present disclosure, the sample scanning unit comprises a laser micrometer. The laser micrometer typically comprises a light emitting unit such as a laser or a light emitting diode (LED) and an imaging unit. The light may be passed through a diffusion unit and a collimator lens before it is irradiated on the sample. The image of a shadow created by the sample may be projected on the imaging unit such as a CCD or CMOS detector, typically via a tele-centric optical system. Based on the received light output from the recording unit, the dimensions of the sample may be determined. One advantage of using a laser micrometer is that it is fast because it may use low-complexity image processing algorithms, such as edge detection, to determine the diameter. An advantage of using a tele-centric optical system is that it may produce images of the same size regardless of shift in image and/or object planes.

In another embodiment of the present disclosure, the sample scanning unit comprises an imaging unit. In this regard, there may be no need for a light emitting unit, a diffusion unit and/or a collimator lens. Furthermore, there may be no need for a tele-centric optical system, and a non-telecentric lens may thus be used instead. An advantage of using an imaging unit with a non-telecentric lens is its low cost.

In a preferred embodiment of the present disclosure, the scanning unit is configured for axial movement parallel to the displacement of said opposed surface(s). In this way, the distance is always the same from the scanning unit and to the sample. Hence, in the case when the scanning unit comprises an imaging unit, i.e. without a tele-centric lens, there may be no need to change focus and the imaging unit may thus need no autofocus. Accordingly, the device may be configured for fast determination of the diameter of the sample, and thus for fast determination of the minimum diameter of the sample.

The scanning unit may however not necessarily need to be configured for axial movement parallel to the displacement of said opposed surface(s). The movement may be at any given angle and even perpendicular to the displacement of said opposed surface(s). In case of a non-telecentric lens being used, a projection error may need to be considered, such that the diameter of the sample may be correctly determined. In case of a tele-centric lens being used, the produced images may be of the same size regardless of the shift in object planes, and therefore there may be no projection errors, implying that a tele-centric lens may be preferred in such configurations.

In another embodiment of the present invention, the sample scanning unit comprises one or more movable/rotatable mirrors. For example, a rotatable mirror may be placed at a position between the sample and the imaging unit. The rotatable mirror may be configured to rotate such that it scans the sample before, during and/or after said controlled axial surface displacement. The one or more movable/rotatable mirrors may be any type of mirrors, in particular planar mirrors, curved mirrors, and/or reflective materials such as gratings. Furthermore, the one or more movable/rotatable mirrors may be micro mirror systems and arrays thereof, in particular micro-electro-mechanical systems (MEMS). One advantage of using micro mirrors is that they are light weight and may be moved relatively fast in comparison to for example a large mirror or in comparison to translating a scanning unit.

Feedback Controller

In one embodiment of the present disclosure, the filament stretching rheometer further comprises force and/or stress determining means, such as a force and/or pressure transducer, for measuring the force and/or pressure exerted on at least one of said opposed surfaces. In this way, a desired pressure and/or force is able to be obtained.

Accordingly, the feedback controller may be configured to control the actuator based on said force and/or pressure.

In one embodiment of the present disclosure, the feedback controller is configured to provide a displacement of the opposed surfaces such that the minimum diameter of the sample increases or decreases exponentially during test. In this way, the strain rate may be kept constant.

In tests, where for example a constant strain rate may not be required, the feedback controller may be configured to provide a displacement of the opposed surfaces such that the minimum diameter of the sample increases or decreases non-exponentially during test.

In some embodiments of the present disclosure, the feedback controller is configured to provide a displacement of the opposed surfaces such that the force per unit area exerted on the sample is constant during test. In this way, the stress may be kept constant.

Various parameters of the measurements may be set depending on the desired rheological or mechanical properties that need to be determined. Also combinations and/or series of parameters may be set depending on the desired rheological or mechanical properties that need to be determined. For example, a constant strain may be followed by a constant strain-rate and/or constant stress.

Motors and Processors

In one embodiment of the present disclosure, the filament stretching rheometer further comprises separate motors for powering the actuator and the sample scanning unit, respectively. In this way, the actuators and sample scanning unit may be able to move independently of each other.

In another embodiment of the present disclosure, the filament stretching rheometer further comprises a data processor configured to determine rheological and/or mechanical properties of a sample based on measurements of sample diameter and force, pressure and/or stress exerted on the sample during test.

Environmentally Controlled Chamber

In one embodiment of the present disclosure, the filament stretching rheometer further comprises an environmentally controlled chamber surrounding the sample. This may be advantageous in that various tests may be performed for well-defined environments. The environmentally controlled chamber may be controlled by an environmental controller such as a temperature controller with heating and/or cooling elements, humidity controller, pressure controller, and/or inert gas flow rate controller. Regardless of the controller, the controller may be configured for monitoring and adjusting the power in order to reach and maintain a desired environment such as a well-defined temperature, flow rate, humidity and/or pressure.

In relation to the second aspect of the present invention, relating to an environmentally controlled chamber, specifically to an environmentally controlled chamber for a filament stretching rheometer, wherein the filament stretching rheometer may be a rheometer as described herein.

Accordingly, the environmentally controlled chamber may be configured for controlling ambient temperature, ambient gas composition, flow rate of ambient gas, ambient humidity and/or ambient pressure of gas inside the chamber.

In a preferred embodiment of the present disclosure, the environmentally controlled chamber is configured for reducing the temperature, T, of said gas inside the chamber from $150°$ C.$<T<300°$ C. to $25°$ C.$<T\leq 150°$ C. In such configuration, it may be possible to expose a sample to a temperature above its melting point and/or its glass transition temperature and go below its melting point and/or its glass transition temperature. For example, among the previously described samples, Polystyrene has a glass transition temperature of approximately $100°$ C., Polymethyl methacrylate has a glass transition temperature of approximately $130°$ C., Polyethylene has a melting temperature of $110°$ C., Polycarbonate has a glass transition temperature of approximately $145°$ C., and Polypropylene has a melting temperature of approximately $165°$ C.

In order to perform quenching tests, it is desired that the temperature is able to rapidly go below the glass transition temperature and/or melting temperature of the sample. Accordingly, the time for reducing the temperature, T, of said gas inside the chamber from $150°$ C.$<T<300°$ C. to $25°$ C.$<T\leq 150°$ C. may be less than 5 seconds, less than 4 seconds, less than 3 second, less than 2 seconds or less than 1 second. The control of the temperature may be facilitated by heaters and coolers. The heaters may consist of induction heating devices, convection heating devices, and/or thermoelectric heating devices. The coolers may comprise thermoelectric cooling devices, refrigerator devices, and/or circulation of cold gas, e.g. air, nitrogen, liquid, and/or oxygen.

Preferably, the environmentally controlled chamber may be configured to be removed from the sample in order to expose said sample to ambient conditions. Preferably, the chamber may be removed from the sample in less than 5 seconds, less than 4 seconds, less than 3 second, less than 2 seconds or less than 1 second. In this way, it may be possible to rapidly reduce the temperature of the sample.

Figure 2:
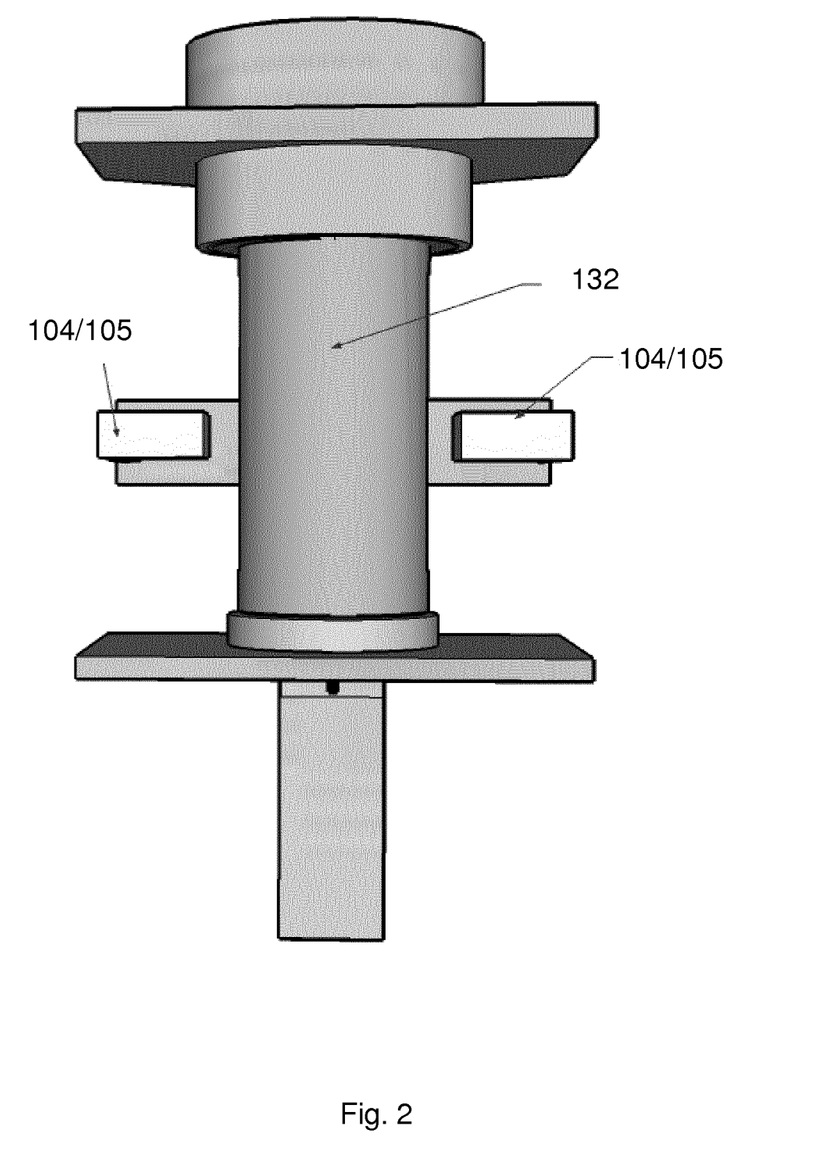
FIG. 2 shows a schematic illustration of one embodiment of the scanning rheometer according to the present disclosure from a front view.

Referring to FIG. 2, the housing 132 is the environmentally controlled chamber. In the illustrated example, the environmentally controlled chamber 132 surrounds the top surface, the bottom surface and the sample. A light source 104 and a detector 105 are configured to measure the diameter of the sample through an optical access 141 in the housing 132 (as seen in FIG. 3).

Figure 3:
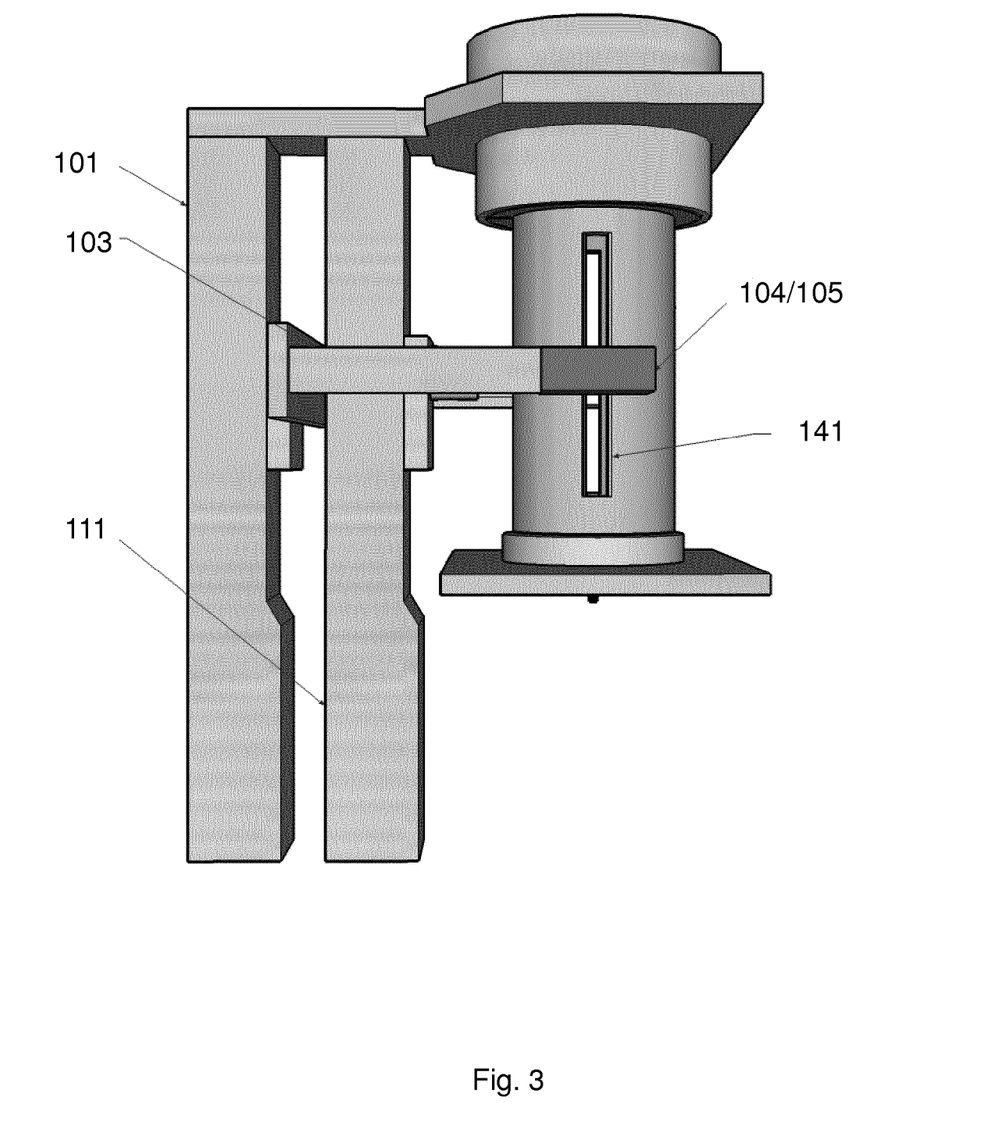
FIG. 3 shows a schematic illustration of one embodiment of the scanning rheometer according to the present disclosure from a side view.

The optical access 141 is shown in FIG. 3, where the environmentally controlled chamber is shown from the side. From this perspective, the motor 101 and the one arm 103 to move the light source 104 or the detector 105 can be seen. A second motor 111 to move the surface(s) holding the sample is also to be seen. In the illustrated example, the environmentally controlled chamber 132 is closed, such that it surrounds the top surface, the bottom surface and the sample.

Figure 4:
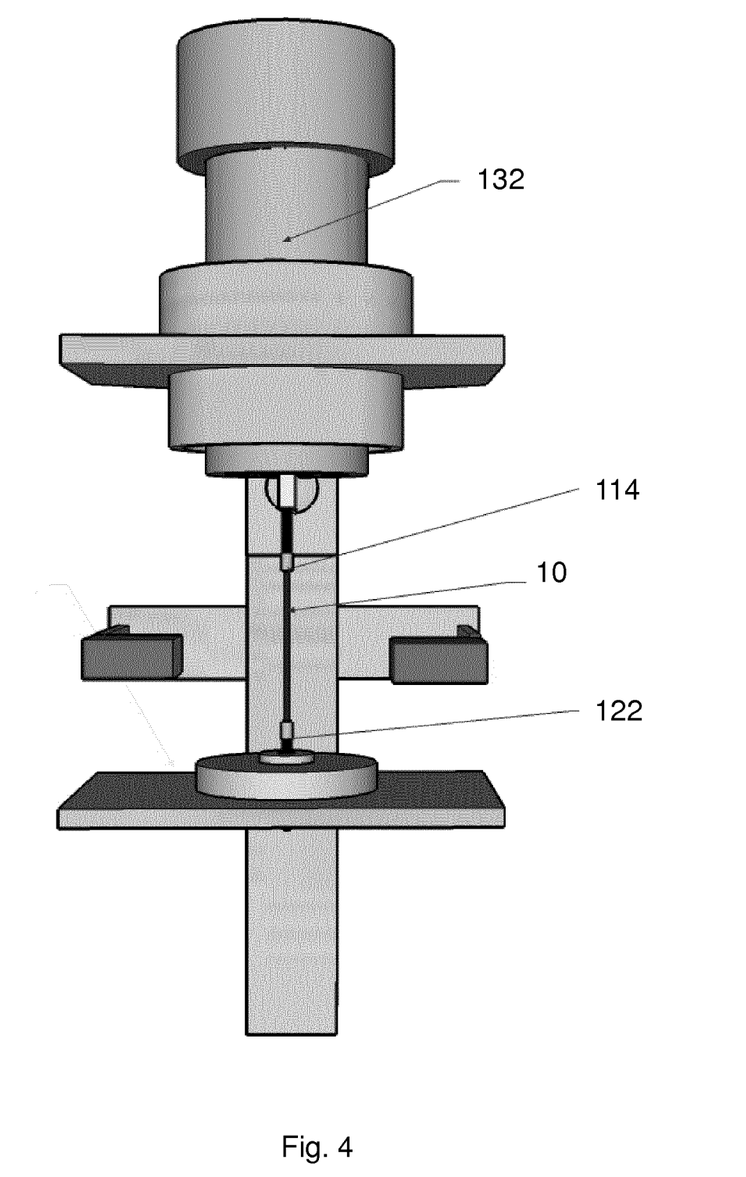
FIG. 4 shows a schematic illustration of one embodiment of the scanning rheometer according to the present disclosure from a front view.

Referring to FIG. 4, the environmentally controlled chamber 132 is removed from the sample in order to expose the sample to ambient conditions. A top surface and 114 and bottom surface 122 are shown together with a stretched sample 10.

Figure 5:
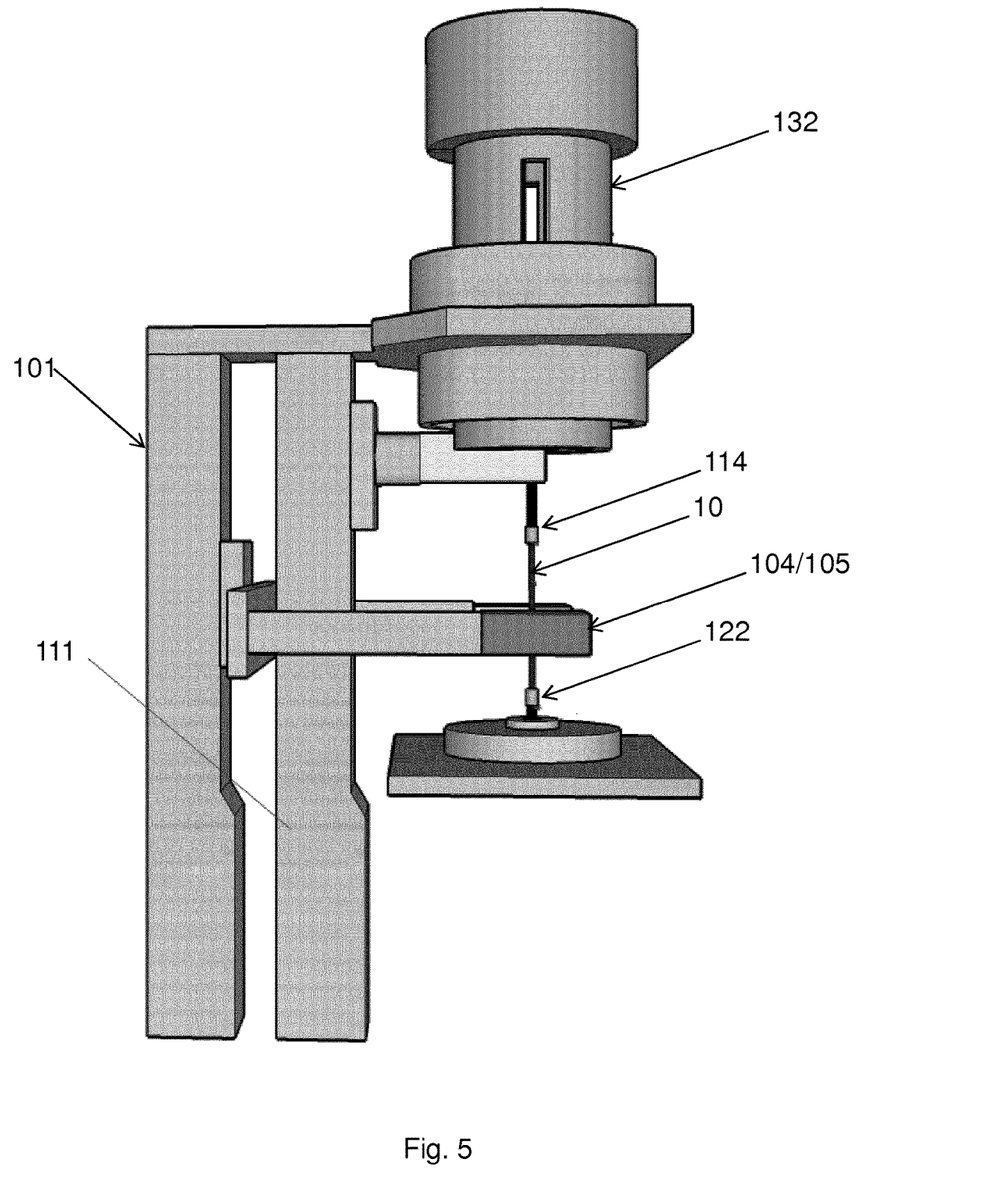
FIG. 5 shows a schematic illustration of one embodiment of the scanning rheometer according to the present disclosure from a side view.

In FIG. 5, the environmentally controlled chamber 132 is shown from the side, where it can be seen that it is removed from the sample in order to expose the sample to ambient conditions.

Controlling the Rheometer

According to the third aspect of the present invention, relating to a method for controlling a filament stretching rheometer, the rheometer may be a rheometer as described herein.

In one embodiment of the present invention, the method further comprising the steps of: positioning said moving sample scanning unit at said starting point, moving said two opposed surfaces towards or away from each other, such that said sample scanning unit moves dependently of said two opposed surfaces from said starting point; and measuring the diameter of said sample during movement of said two opposed surfaces. Dependently being e.g. maintaining a fixed relationship of the axial positions of the sample scanning unit and the two opposed surfaces.

Further Details of the Invention

The invention will now be described in further details with reference to the following items:

1. A filament stretching rheometer for measuring rheological and/or mechanical properties of a sample, comprising:
   a pair of opposed surfaces for holding the sample therebetween,
   an actuator configured to provide a controlled axial displacement of at least one of said opposed surfaces, and
   a sample scanning unit for measuring a diameter of said sample, the sample scanning unit configured for measuring said sample diameter at an axial position controlled independently of the displacement of the opposed surfaces.
2. The filament stretching rheometer according to item 1, further comprising a feedback controller configured to control the actuator based on input from the sample scanning unit.
3. The filament stretching rheometer according to any of the preceding items, wherein said sample scanning unit is configured for obtaining a diameter profile of the sample.
4. The filament stretching rheometer according to any of the preceding items, wherein said sample scanning unit is configured to determine the minimum diameter of the sample before, during, and/or after said controlled axial surface displacement.
5. The filament stretching rheometer according to any of the preceding items, wherein said sample scanning unit is configured for moving independently of the axial displacement of the opposed surface(s).
6. The filament stretching rheometer according to any of the preceding items, wherein said scanning unit is configured for axial movement parallel to the displacement of said opposed surface(s).
7. The filament stretching rheometer according to any of the preceding items, wherein said scanning unit is configured for operation before, during and/or after the displacement of said opposed surface(s).
8. The filament stretching rheometer according to any of the preceding items, wherein said sample scanning unit comprises a laser micrometer.
9. The filament stretching rheometer according to any of the preceding items, wherein said sample scanning unit comprises an imaging device.
10. The filament stretching rheometer according to any of the preceding items, wherein said sample scanning unit comprises one or more movable/rotatable mirrors.
11. The filament stretching rheometer according to any of the preceding items, further comprising force and/or stress determining means, such as a force and/or pressure transducer, for measuring the force and/or pressure exerted on at least one of said opposed surfaces.
12. The filament stretching rheometer according to item 11, wherein said feedback controller is configured to control the actuator based on said force and/or pressure.
13. The filament stretching rheometer according to any of the preceding items 2 to 12, wherein said feedback controller is configured to provide a displacement of the opposed surfaces such that the minimum diameter of the sample increases or decreases exponentially during test.
14. The filament stretching rheometer according to any of the preceding items 2 to 12, wherein said feedback controller is configured to provide a displacement of the opposed surfaces such that the minimum diameter of the sample increases or decreases non-exponentially during test.
15. The filament stretching rheometer according to any of the preceding items 2 to 13, wherein said feedback controller is configured to provide a displacement of the opposed surfaces such that force per unit area exerted on the sample is constant during test.
16. The filament stretching rheometer according to any of the preceding items, further comprising an environmentally controlled chamber surrounding the sample.
17. The filament stretching rheometer according to any of the preceding items, wherein said environmentally controlled chamber is configured for controlling ambient temperature, ambient gas composition, flow rate of ambient gas, ambient humidity and/or ambient pressure of gas inside the chamber.
18. The filament stretching rheometer according to any of the preceding items, wherein said environmentally controlled chamber is configured for reducing the temperature, T, of said gas inside the chamber from 150° C.<T<300° C. to 25° C.<T≤150° C.
19. The filament stretching rheometer according to any of the preceding items, wherein the time for reducing the temperature, T, of said gas inside the chamber from 150° C.<T<300° C. to 25° C.<T≤150° C. is less than 5 seconds, less than 4 seconds, less than 3 second, less than 2 seconds or less than 1 second.
20. The filament stretching rheometer according to any of the preceding items, wherein said environmentally controlled chamber is configured to be removed from said sample in order to expose said sample to ambient conditions.
21. The filament stretching rheometer according to any of the preceding items, further comprising separate motors for powering the actuator and the sample scanning unit, respectively.
22. The filament stretching rheometer according to any of the preceding items, further comprising a data processor configured to determine rheological and/or mechanical properties of a sample based on measurements of sample diameter and force, pressure and/or stress exerted on the sample during test.

The invention claimed is:

1. A filament stretching rheometer for measuring rheological and/or mechanical properties of a sample, comprising:
    a pair of opposed surfaces configured to hold the sample therebetween;
    an actuator configured to provide a controlled axial displacement of at least one of said opposed surfaces;
    a sample scanning unit configured to measure a diameter of said sample; and
    an environmentally controlled chamber comprising a surface for surrounding the sample, the environmentally controlled chamber configured to control environmental conditions of the sample and configured such that the sample can be instantly exposed to a different set of conditions by displacing the surface, thereby removing the entire surface from the sample;
    wherein said entire surface can be removed from said sample by vertically displacing said entire surface,
    wherein the environmentally controlled chamber is a housing, and
    wherein the filament stretching rheometer further comprises a holder for the housing, and wherein the housing is configured to slide vertically inside the holder.

2. The filament stretching rheometer according to claim 1, wherein the environmentally controlled chamber is configured to correct at least one of the following: ambient temperature, ambient gas composition, flow rate of ambient gas, ambient humidity, and ambient pressure of gas inside the chamber.

3. The filament stretching rheometer according to claim 1, wherein the environmentally controlled chamber comprises a temperature controller having a heating element, a cooling element, or both.

4. The filament stretching rheometer according to claim 3, wherein the heating element is an induction heating device, a convection heating device, a thermoelectric heating device, or combination thereof.

5. The filament stretching rheometer according to claim 3, wherein the cooling element is a thermoelectric cooling device, a refrigerator device, a circulation device configured to produce a circulation of cold gas, or combination thereof.

6. The filament stretching rheometer according to claim 1, wherein the environmentally controlled chamber further comprises a humidity controller.

7. The filament stretching rheometer according to claim 1, wherein the environmentally controlled chamber further comprises a pressure controller.

8. The filament stretching rheometer according to claim 1, wherein the environmentally controlled chamber further comprises an inert gas flow rate controller.

9. The filament stretching rheometer according to claim 1, wherein an insulating surface is part of the housing, and wherein the housing further comprises a top surface.

10. The filament stretching rheometer according to claim 9, wherein the housing is cylindrical.

11. The filament stretching rheometer according to claim 1, wherein the surface comprises an optical access and optical exit in an arrangement allowing the diameter of the sample to be measured optically across and inside the environmentally controlled chamber.

12. The filament stretching rheometer according to claim 11, wherein the optical access and optical exit are elongated windows.

13. The filament stretching rheometer according to claim 1, wherein a top surface of the pair of opposed surfaces is connected to a connector that is configured to be operated inside the environmentally controlled chamber and through a side of the surface.

* * * * *